(12) United States Patent
Desi Reddy et al.

(10) Patent No.: US 11,702,440 B2
(45) Date of Patent: Jul. 18, 2023

(54) PHARMACEUTICAL POLYMORPHS OF MOLNUPIRAVIR

(71) Applicant: OPTIMUS DRUGS (P) LTD, Telangana (IN)

(72) Inventors: Srinivas Reddy Desi Reddy, Hyderabad (IN); Subba Reddy Peketi, Hyderabad (IN)

(73) Assignee: Optimus Drugs Private Limited, Telangana (IN)

( * ) Notice: Subject to any disclaimer, the term of this patent is extended or adjusted under 35 U.S.C. 154(b) by 0 days.

(21) Appl. No.: 17/405,256

(22) Filed: Aug. 18, 2021

(65) Prior Publication Data

US 2022/0185840 A1  Jun. 16, 2022

(51) Int. Cl.
*C07H 19/06* (2006.01)
*C07H 19/067* (2006.01)

(52) U.S. Cl.
CPC ........... *C07H 19/06* (2013.01); *C07H 19/067* (2013.01)

(58) Field of Classification Search
None
See application file for complete search history.

(56) References Cited

U.S. PATENT DOCUMENTS

2021/0220286 A1* 7/2021 Garcia Jimenez ... A61K 31/404

FOREIGN PATENT DOCUMENTS

WO  WO-2022047229 A1 * 3/2022

* cited by examiner

*Primary Examiner* — Traviss C McIntosh, III
(74) *Attorney, Agent, or Firm* — IP Pundit LLC (57) ABSTRACT

The present invention provides a crystalline and an amorphous form of a Molnupiravir and methods of making the crystalline form and amorphous form of Molnupiravir.

6 Claims, 5 Drawing Sheets

PHARMACEUTICAL POLYMORPHS OF MOLNUPIRAVIR

FIELD OF THE INVENTION

This present invention provides a crystalline and an amorphous form of a Molnupiravir and methods of making the crystalline form and amorphous form of Molnupiravir.

BACKGROUND OF THE INVENTION

Molnupiravir (development codes MK-4482 and EIDD-2801) is an experimental antiviral drug which is orally active (can be taken orally) and was developed for the treatment of influenza. It is a prodrug of the synthetic nucleoside derivative N4-hydroxycytidine, and exerts its antiviral action through introduction of copying errors during viral RNA replication. Activity has also been demonstrated against coronaviruses including SARS, MERS and SARS-CoV-2.

The drug was developed at Emory University by the university's drug innovation company, Drug Innovation Ventures at Emory (DRIVE). It was then acquired by Miami-based company Ridgeback Biotherapeutics, who later partnered with Merck & Co. to develop the drug further.

After being found to be active against SARS-CoV-2 in March 2020, Molnupiravir was tested in a preliminary human study for "Safety, Tolerability, and Pharmacokinetics" in healthy volunteers in the UK and US. In June 2020, Ridgeback Biotherapeutics announced it was moving to Phase II trials to test the efficacy of the drug as a treatment for COVID-19. Two trials of small numbers of hospitalized and non-hospitalized patients in the US and the UK were underway in July. In late July 2020, and without yet releasing any medical data, Merck, which had been partnering with Ridgeback Biotherapeutics on developing the drug, announced its intention to move Molnupiravir to late stage trials beginning in September 2020. On Oct. 19 2020, Merck began a one-year Stage 2/3 trial focused on hospitalized patients.

PCT publication no. WO2019113462 and herein identified as a compound of Molnupiravir. The compound of Molnupiravir is represented by the structure:

Molnupiravir (Formula-I)

PCT publication no. WO2019113462 discloses a pharmaceutical composition comprising a pharmaceutically acceptable excipient and Molnupiravir.

Further WO 2019113462 discloses a synthesis of Molnupiravir, which comprises uridine (VI) was treated with sulfuric acid in presence of acetone and trimethylamine to produce compound of formula (V), followed by esterification with isobutyric anhydride in presence of 4-dimethylaminopyridine (DMAP) and triethylamine (NEt3) to produce compound of formula (IV). The compound of formula (IV) was reacted with 1,2,4-triazole in presence of N,N-diethylethanamine, MeCN and phosphorous oxychloride (POCl3) to produce compound of formula (III). The compound of formula (III) was treated with hydroxylamine in presence of isopropyl alcohol (IPA) to produce compound of formula (II). The compound of formula (II) was deprotected with formic acid to obtain EIDD-2801 (Molnupiravir-I), followed by isolation from MTBE/IPA. The above process is schematically shown as below, Crystalline form of Molnupiravir and amorphous form of Molnupiravir thereof are not known anywhere.

Further work in developing selective Molnupiravir led to the surprising discovery that certain crystalline and amorphous form of this compound exhibit better stability.

However, there is no publication that discloses a crystalline and amorphous form of Molnupiravir. So, our inventors have developed a method for the preparation of crystalline and amorphous form of Molnupiravir. The crystalline and amorphous form of Molnupiravir of the present invention may remarkably stable and therefore may have an excellent pharmacological effect, making it useful as an active ingredient for preventing or treating a disease selected from the group consisting of coronavirus disease (COVID-19) and anti-viral disease.

SUMMARY OF THE INVENTION

The present invention provides a crystalline form of Molnupiravir.

The present invention provides an amorphous form of Molnupiravir.

The present invention provides a process for the preparation of crystalline form of Molnupiravir.

The present invention provides a process for the preparation of amorphous form of Molnupiravir.

The present invention provides a crystalline and an amorphous form of a Molnupiravir and methods of making the crystalline form and amorphous form of Molnupiravir.

In one embodiment of the present invention provides a crystalline form of Molnupiravir.

The second embodiment of the present invention provides an amorphous form of Molnupiravir.

The third embodiment of the present invention provides a process for the preparation of pure crystalline form of Molnupiravir, which comprises the steps of:
a) Molnupiravir is dissolved in a solvent at 50-85° C.,
b) optionally treating the above solution in step-a) with carbon,
c) optionally adding a second solvent to the solution obtained in step-a) or step b),
d) cooling the mixture to 25-30° C., and
e) filtering the precipitated solid to obtain pure crystalline form of Molnupiravir.

The fourth embodiment of the present invention provides a process for the preparation of pure amorphous form of Molnupiravir, which comprises the steps of:
a) Molnupiravir is dissolved in a solvent at 50-80° C.,
b) optionally treating the above solution in step-a) with carbon,
c) optionally adding a second solvent to the solution obtained in step-a) or step b),
d) distilled out the solvent obtained in step-a) or step-b), and
e) isolate the pure amorphous form of Molnupiravir.

The present invention is also provide amorphous form by Spray drying or Lyophilization techniques The fifth embodiment of the present invention provides a pharmaceutical composition comprising an effective amount of a crystalline form and amorphous form of Molnupiravir.

DETAILED DESCRIPTION OF THE INVENTION

The present invention provides a crystalline and an amorphous form of a Molnupiravir and methods of making the crystalline form and amorphous form of Molnupiravir.

The one embodiment of the present invention provides a crystalline form of Molnupiravir.

According to the embodiment of the present invention, the crystalline form of Molnupiravir has an X-ray powder diffraction (XRPD) pattern including diffraction peaks at 3.3°, 6.6°, 17.0°, 17.3°, 18.1°, 20.3°, 20.6°, 21.3°, 21.4° and 28.1° (2θ±0.2°).

According to the embodiment of the present invention, the crystalline form of Molnupiravir has an X-ray powder diffraction (XRPD) pattern including diffraction peaks at 3.26°, 6.52°, 16.99°, 17.22°, 18.04°, 20.30°, 20.59°, 21.21°, 21.36° and 28.03° (2θ±0.2°).

According to the embodiment of the present invention, in addition to XRPD diffraction peaks at 3.3°, 6.6°, 17.0°, 17.3°, 18.1°, 20.3°, 20.6°, 21.3°, 21.4° and 28.1° (2θ±0.2°), the crystalline form of Molnupiravir may have an XRPD pattern including one or more diffraction peaks selected from the group consisting of 13.1°, 16.4°, 19.5°, 19.9°, 23.4°, 28.4°, 28.9°, 30.2°, 31.6°, and 34.0° (2θ±0.2°).

According to the embodiment of the present invention, in addition to XRPD diffraction peaks at 3.26°, 6.52°, 16.99°, 17.22°, 18.04°, 20.30°, 20.59°, 21.21°, 21.36° and 28.03° (2θ±0.2°), the crystalline form of Molnupiravir may have an XRPD pattern including one or more diffraction peaks selected from the group consisting of 13.06°, 16.35°, 19.41°, 19.87°, 23.33°, 28.40°, 28.90°, 30.11°, 31.58°, and 33.91° (2θ±0.2°).

According to the embodiment of the present invention, the crystalline form of Molnupiravir may have an XRPD pattern including diffraction peaks at 3.26°, 6.52°, 13.06°, 16.35°, 16.99°, 17.22°, 18.04°, 19.41°, 19.87°, 20.30°, 20.59°, 21.21°, 21.36°, 23.33°, 28.03°, 28.40°, 28.90°, 30.11°, 31.58°, and 33.91° (2θ±0.2°). as described in Table 1 below.

TABLE 1

| Crystalline form of Molnupiravir | |
|---|---|
| 2-theta (°) | Intensity % |
| 3.26 | 100 |
| 6.52 | 2.52 |
| 13.06 | 0.61 |
| 16.35 | 0.65 |
| 16.99 | 3.85 |
| 17.22 | 3.07 |
| 18.04 | 1.53 |
| 19.41 | 0.99 |
| 19.87 | 0.73 |
| 20.30 | 1.19 |
| 20.59 | 1.47 |
| 21.21 | 2.89 |
| 21.36 | 2.30 |
| 23.33 | 0.50 |
| 28.03 | 2.07 |
| 28.40 | 0.97 |
| 28.90 | 0.67 |
| 30.11 | 0.53 |
| 31.58 | 0.52 |
| 33.91 | 0.51 |

Figure 1:
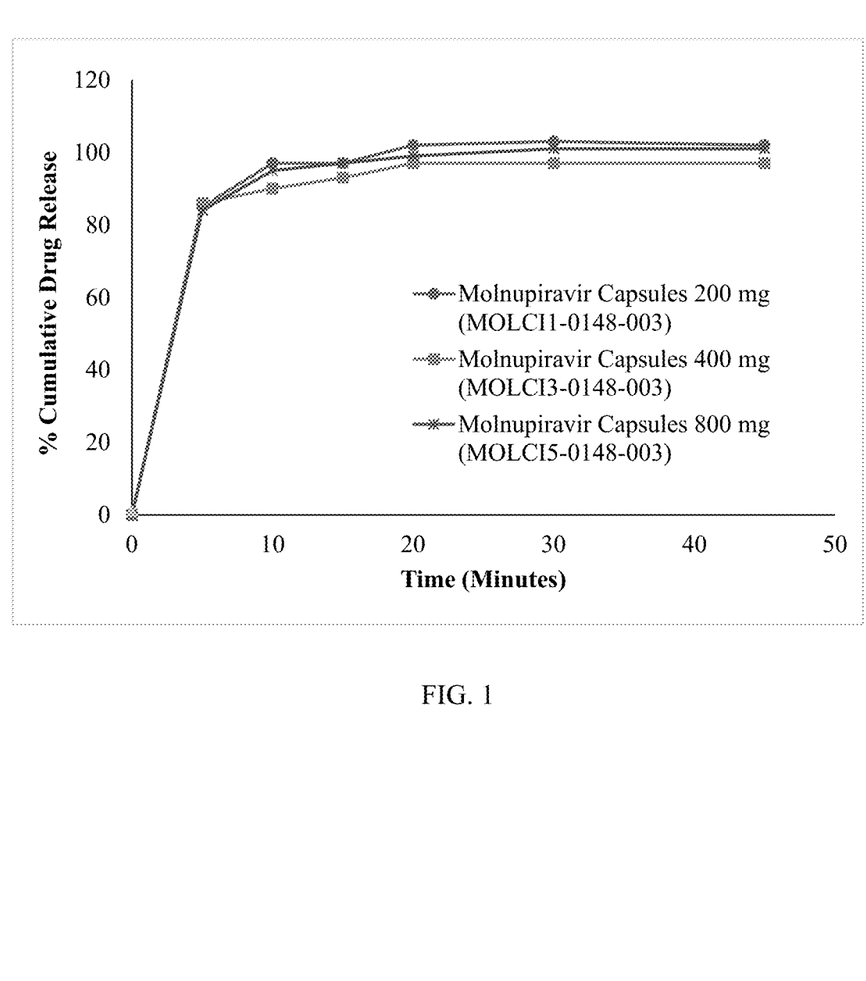
FIG. 1 illustrates the dissolution profile of Molnupiravir capsules.
Figure 2:
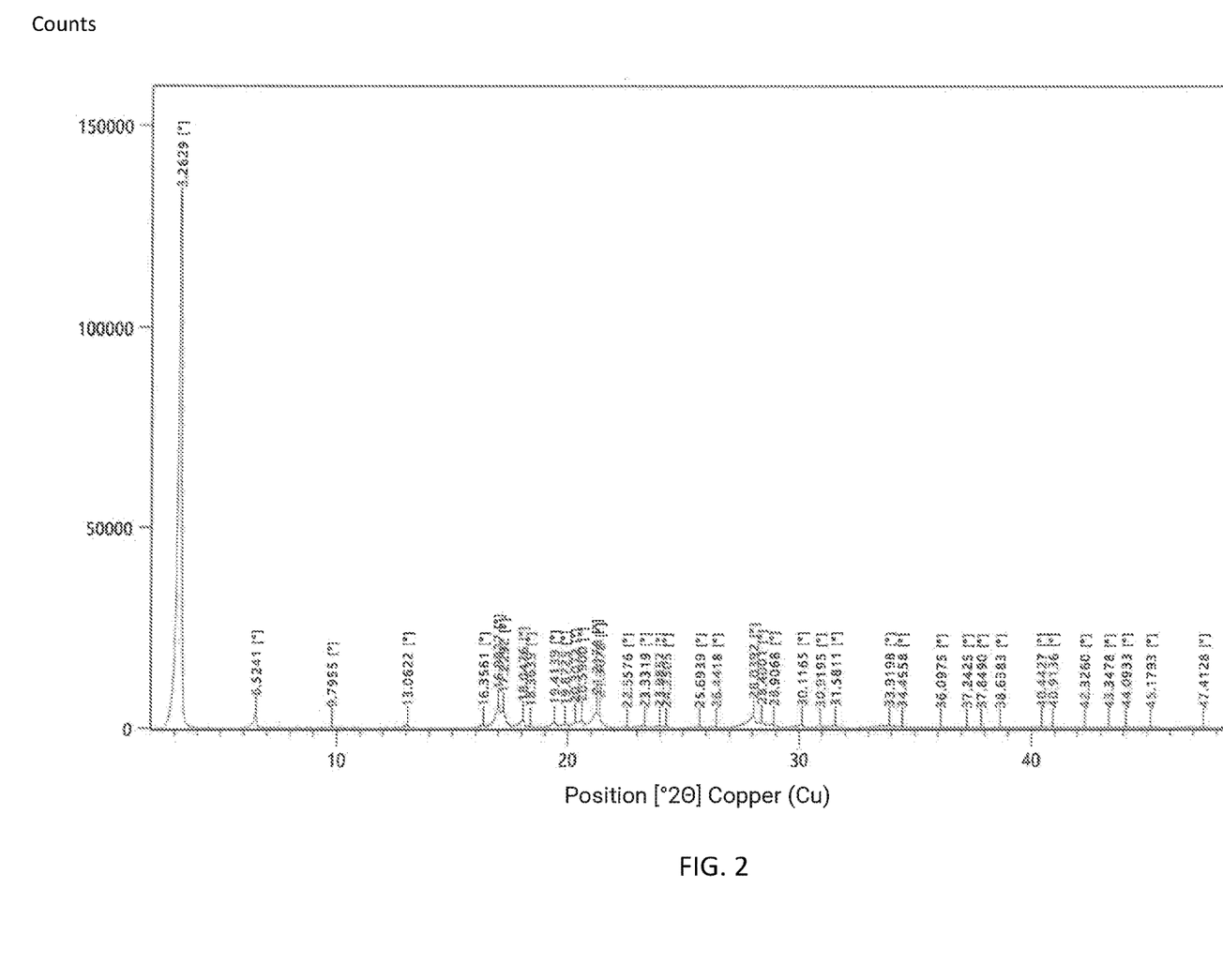
FIG. 2 illustrates the X-ray powder diffraction pattern of a crystalline form of Molnupiravir and was recorded on a Bruker™ D8 diffractometer using CuKα radiation ($\lambda$=1.54060 Å).

According to the embodiment of the present invention, the crystalline form of Molnupiravir may have an XRPD pattern of FIG. 2.

According to the embodiment of the present invention, the XRPD pattern might have been be measured by using Cu—$K_\alpha$ or Cu—$K_\beta$ radiation, more particularly, Cu—$K_\alpha$ radiation, even more particularly, Cu—$K_{\alpha1}$, Cu—$K_{\alpha2}$, Cu—$K_\beta$, or Cu—$_{\alpha1}$ and Cu—$K_{\alpha2}$ radiation. For example, the XRPD pattern might have been be measured by using Cu—$K_\alpha$ radiation.

According to the embodiment of the present invention, the graph of differential scanning calorimetry (DSC) of the crystalline form of Molnupiravir may have an endothermic peak at approximately 156-166° C. at heating rate of 5.00° C./min.

Figure 3:
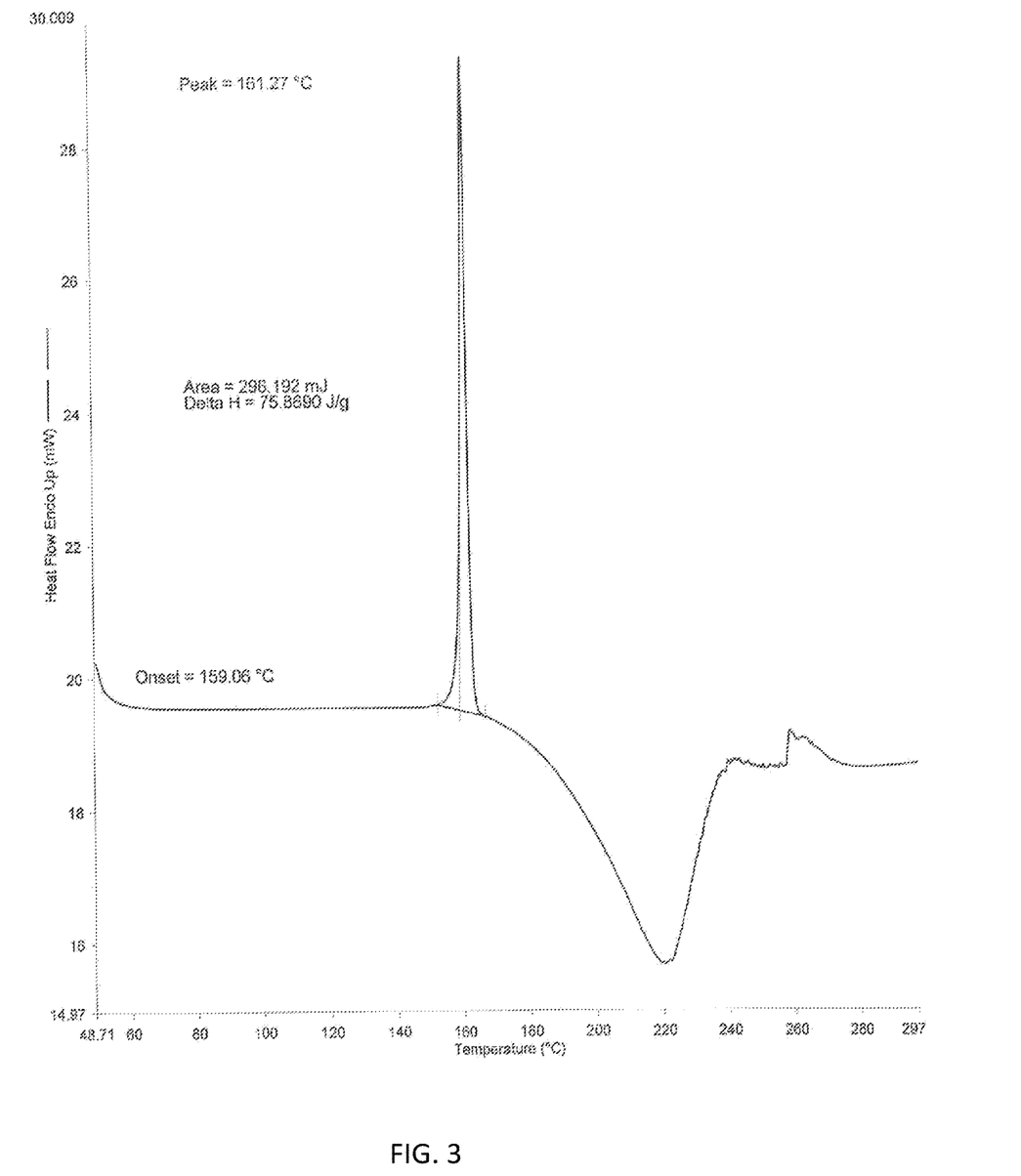
FIG. 3 illustrates the differential scanning calorimetry (DSC) of a crystalline form of Molnupiravir and was recorded on a Perkin Elmer Diamond DSC instrument with aluminium pan (Perkin Elmer, type BO14-3018); heating rate 50° to 300° at 5° C./min.

According to the embodiment of the present invention, the graph of differential scanning calorimetry (DSC) of the crystalline form of Molnupiravir may be the same as FIG. 3.

Figure 4:
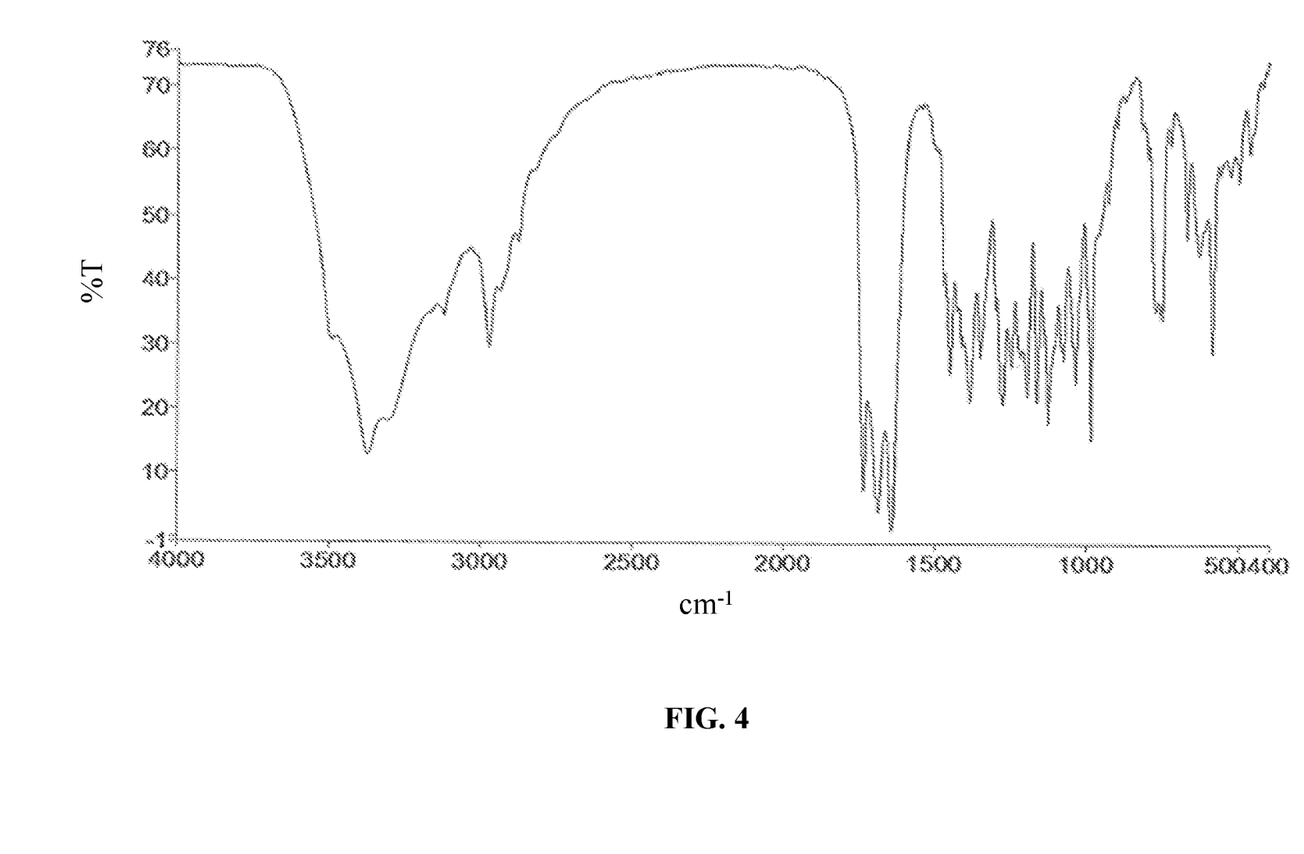
FIG. 4 illustrates FT-IR of a crystalline form of Molnupiravir.

According to the embodiment of the present invention, FT-IR spectrum of the crystalline form of Molnupiravir may be the same as FIG. 4.

According to the embodiment of the present invention, particle size distribution of the crystalline form of Molnupiravir may have from $D_{10} \leq 10$ μm, $D_{50} \leq 200$ μm, and $D_{90} \leq 300$ μm, the particle size of the crystalline form of Molnupiravir may have confirmed very fine. The crystal form can proceed directly to the formulation without further processing, such as milling.

The crystalline form of Molnupiravir of the present invention may have low hygroscopicity, may be remarkably stable at the accelerated conditions and long-term storage conditions and may be stably maintained with no change in content for long term. Accordingly, the crystalline form of Molnupiravir of the present invention may be obtained as a raw material having high purity and may maintain high purity and its crystalline form for long term even when stored for long periods of time.

In addition, the crystalline form of Molnupiravir of the present invention may be obtained in high purity and yield and may be therefore easily applicable for mass production and commercial purposes.

The crystalline form of Molnupiravir of the present invention may remarkably stable and therefore may have an excellent pharmacological effect, making it useful as an active ingredient for preventing or treating a disease selected from the group consisting of coronavirus disease (COVID-19) and anti-viral disease.

The crystalline form of Molnupiravir may be formulated into a form selected from the group consisting of powder, granule, tablet, capsule, suspension, emulsion, syrup, aerosol, ointment, cream, suppository, eye drop, and injection according to conventional formulation methods recognized by those skilled in the art.

The second embodiment of the present invention provides an amorphous form of Molnupiravir.

Figure 5:
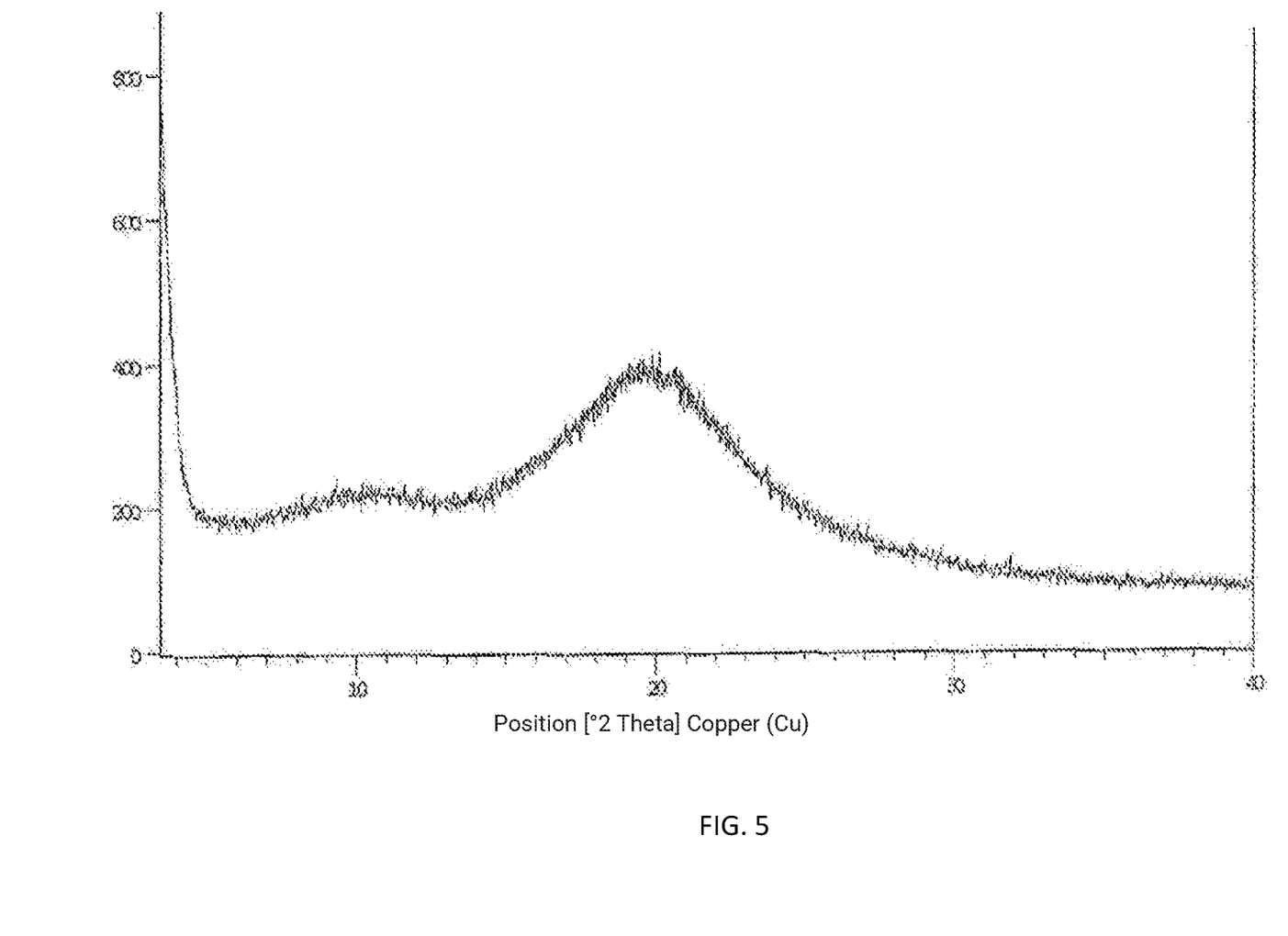
FIG. 5 illustrates the X-ray powder diffraction pattern of an amorphous form of Molnupiravir.

According to the embodiment of the present invention, the amorphous form of Molnupiravir may have an XRPD pattern of FIG. 5.

The amorphous form of Molnupiravir of the present invention may have low hygroscopicity, may be remarkably stable at the accelerated conditions and long-term storage conditions and may be stably maintained with no change in content for long term. Accordingly, the amorphous form of Molnupiravir of the present invention may be obtained as a raw material having high purity and may maintain high purity and its amorphous form for long term even when stored for long periods of time.

In addition, the amorphous form of Molnupiravir of the present invention may be obtained in high purity and yield and may be therefore easily applicable for mass production and commercial purposes.

The amorphous form of Molnupiravir of the present invention may remarkably stable and therefore may have an excellent pharmacological effect, making it useful as an active ingredient for preventing or treating a disease selected from the group consisting of coronavirus disease (COVID-19) and anti-viral disease.

The amorphous form of Molnupiravir may be formulated into a form selected from the group consisting of powder, granule, tablet, capsule, suspension, emulsion, syrup, aerosol, ointment, cream, suppository, eye drop, and injection according to conventional formulation methods recognized by those skilled in the art.

The third embodiment of the present invention provides a process for the preparation of pure crystalline form of Molnupiravir, which comprises the steps of:
 a) Molnupiravir is dissolved in a solvent at 50-85° C.,
 b) optionally treating the above solution in step-a) with carbon,
 c) optionally adding a second solvent to the solution obtained in step-a) or step b),
 d) cooling the mixture to 25-30° C., and
 e) filtering the precipitated solid to obtain pure crystalline form of Molnupiravir.

According to the embodiment of the present invention, it provides purification process for the preparation of crystalline form of Molnupiravir, which comprises the crude compound of Molnupiravir is dissolved in solvent at 50-85° C. and stir 10-40 min to get clear solution, optionally further added charge activated carbon and stir for 5-10 min at suitable temperature. Filter the mass wash with solvent, heat the reaction mass at 60-90° C. and stir for 10-45 min then get a clear solution. The reaction mass is cooled to 20-30° C. and stir for 10 min-2 hours to get a solid. The resultant filtrate mass wash with solvent and the wet material is dried at 45-80° C. for 6-8 hours to obtain pure crystalline form of Molnupiravir.

The term "pure" refers to the compound obtained according to the present inventions is having purity >98% by HPLC, preferably >99% by HPLC, more preferably 99.5% by HPLC and having chiral purity >99% by HPLC, preferably >99.5% by HPLC and more preferably >99.81% by HPLC According to the embodiment of the present invention, Solvent in step-a) is selected from alcohol solvents, ester solvents, halogenated hydrocarbons solvents or mixtures thereof; the suitable temperature is 25° C. to reflux temperature of the solvent used;

The second solvent in step-c) is ethers solvent, hydrocarbon solvents;

The temperature in step-d) is about −5° C. to 30° C.

wherein the step a) solvent is selected from alcohols such as methanol, ethanol, propanol, butanol, n-propyl alcohol, isopropyl alcohol, and t-butyl alcohol; esters such as ethylacetate, methylacetate, butyl acetate, isopropyl acetate, methoxy ethyl acetate; halogenated hydrocarbons such as chloroform, dichloromethane or water and/or mixture thereof.

wherein the step c) solvent is selected from ethers such as methyl tertiary butyl ether, diethyl ether, tetrahydrofuran, dioxane; hydrocarbon solvents such as hexane, toluene xylene or water.

The fourth embodiment of the present invention provides a process for the preparation of pure amorphous form of Molnupiravir, which comprises the steps of:
a) Molnupiravir is dissolved in a solvent at 50-80° C.,
b) optionally treating the above solution in step-a) with carbon,
c) optionally adding a second solvent to the solution obtained in step-a) or step b),
d) distilled out the solvent obtained in step-a) or step-b), and
e) isolate the pure amorphous form of Molnupiravir.

According to the embodiment of the present invention, it provides purification process for the preparation of amorphous form of Molnupiravir, which comprises the crude compound of Molnupiravir is dissolved in solvent at 50-80° C. and distilled out completely till solid precipitates, add solvent and allow to cool at room temperature for 3-5 hours. The resultant solid was filtered, washed with solvent and dried at 45-60° C. for 10-20 hours to obtain pure amorphous form of Molnupiravir.

The term "pure" refers to the compound obtained according to the present inventions is having purity >98% by HPLC, preferably >99% by HPLC, more preferably 99.5% by HPLC and having chiral purity >99% by HPLC, preferably >99.5% by HPLC and more preferably >99.75% by HPLC According to the embodiment of the present invention, Solvent in step-a) is selected from alcohol solvents, ester solvents, halogenated hydrocarbons solvents or mixtures thereof; the suitable temperature is 25° C. to reflux temperature of the solvent used;

The second solvent in step-c) is ethers solvent, hydrocarbon solvents;

wherein the step a) solvent is selected from alcohols such as methanol, ethanol, propanol, butanol, n-propyl alcohol, isopropyl alcohol, and t-butyl alcohol; esters such as ethylacetate, methylacetate, butyl acetate, isopropyl acetate, methoxy ethyl acetate; halogenated hydrocarbons such as chloroform, dichloromethane or water and/or mixture thereof, wherein the step c) solvent is selected from ethers such as methyl tertiary butyl ether, diethyl ether, tetrahydrofuran, dioxane, hydrocarbon solvents such as hexane, toluene Xylene or water.

The present invention is also providing amorphous form by Spray drying or Lyophilization techniques.

The fifth embodiment of the present invention provides a pharmaceutical composition comprising an effective amount of a crystalline form and amorphous form of Molnupiravir.

We have conducted Repeated Dose 28-Day Oral Toxicity Study of Molnupiravir in Wistar Rats and New Zealand White Rabbits.

In-Vitro Dissolution Studies:

Dissolution study of test product Molnupiravir Capsules 200 mg, 400 mg 800 mg was performed in order to understand % dissolution in release dissolution media. The dissolution media used for the test is 900 ml of 0.1 NHCl at 50 RPM with paddle.

Bio-Studies

Single and multiple doses of Molnupiravir were evaluated in this first-in-human, phase 1, 20 randomized, double-blind, placebo-controlled study in healthy volunteers, which included 21 evaluation of the effect of food on pharmacokinetics. Eligible subjects were randomized in a 3:1 ratio to either study drug or placebo in the single- and multiple-ascending-dose parts of the study. Each cohort comprised 8 subjects, with single oral doses of 50 to 1600 mg administered in the single-ascending-dose part and twice-daily (BID) 107 doses of 50 to 800 mg administered for 5.5 days in the multiple-ascending-dose part. Subjects were followed for 14 days following completion of dosing for assessments of safety, tolerability, and pharmacokinetics. Subjects in the food-effect evaluation were randomized in a 1:1 ratio to either 200 mg Molnupiravir in the fed state followed by 200 mg Molnupiravir in the fasted state, or vice versa, with a 14-day washout period between doses. A capsule formulation was used in all parts of the study, with the exception of single ascending doses ≤800 mg, where an oral solution formulation was used.

On Day 1, when assessed using the power model, mean $C_{max}$ and $AUC_{inf}$ increased in an approximately dose-proportional manner. However, the upper bound of the 90% confidence interval for $C_{max}$ was slightly below unity and the lower bound of the 90% confidence interval for $AUC_{inf}$ was slightly above unity (Table 2). On Day 6, mean Cmax increased in a dose proportional manner, with the 90% confidence interval containing unity. Similarly, mean $AUC_\tau$ increased in an approximately dose-proportional manner; however, the lower bound of the 90% confidence interval was slightly above unity Dissolution Profiles:

TABLE 2

| Time Points | % Drug release of Molnupiravir | | |
|---|---|---|---|
| (in min) | 200 mg | 400 mg | 800 mg |
| 5 | 85 | 86 | 84 |
| 10 | 97 | 90 | 95 |
| 15 | 97 | 93 | 97 |
| 20 | 102 | 97 | 99 |
| 30 | 103 | 97 | 101 |
| 45 | 102 | 97 | 101 |

The process details of the invention are provided in the examples given below, which are provided by way of illustration only and therefore should not be construed to limit the scope of the invention.

EXAMPLES

Example 1

Process of Molnupiravir

Charge Ethyl acetate (100 ml), 2',3'-O-(1-methylethylidene)-4-oxime-5'-(2-methyl propanoate) Uridine (10.0 gm) and purified water (1.0 ml) into RBF, followed by addition of hydrochloric acid (2.70 gm) at 25-30° C. and allow to stir at 50-55° C. for 2-3 hours. After completion of the reaction, Cool the mass temperature to 25-30° C., adjust the reaction mass pH to 7.5-8.5 with 10% Sodium carbonate solution (50.0 ml) and stir for 15-20 min to separate the two layers. The obtain ethyl acetate layer was wash with 30% sodium chloride solution and water (20 ml), The resultant Ethyl acetate layer was concentrated under vacuum to get crude Molnupiravir.

Example 2

Crystalline of Molnupiravir

Crude Molnupiravir (50 gm) was dissolved Ethyl acetate, added charge activated carbon (2.0%) and stir for 10-15 min at room temperature and filter the mass through hyflo bed. Wash the hyflo bed with ethyl acetate (1.0 volume). Take the total filtered mass into flask. Concentrate the ethyl acetate layer at below 60° C. under reduced pressure and degas the mass at the same temperature under vacuum. Charge ethyl acetate (5.0 volumes) into mass and stir the mass for 10-15 min at 55-60° C. Cool the mass to room temperature and stir the mass for 60-120 min. Filter the material and wash the material with ethyl acetate (1.0 volume). Suck dry the material for 15-20 min. Dry the material at 60-65° C. for 8-10 hours to get the pure material.

Yield: 93% (46.5 gm)
Purity: 99.9%

Example 3

Take the purified water (20.0 ml) and the crude Molnupiravir (10.0 gm) into RBF. Raise the mass temperature to 60-65° C. and stir the mass for 10-15 min to dissolve the material completely. Cool the mass temperature to 25-30° C. and stir the mass for 45-60 min. Further cool the mass temperature to 0-5° C. and stir the mass for 20-30 min. Filter the material and wash the material with chilled purified water (2.5 ml). Suck dry the material for 15-20 min. Dry the material at 60-65° C. for 8-10 hours to get the pure material.

Yield: 90% (9 gm)
Purity: 99.93%

Example 4

Crude wet Molnupiravir (91.0 gm) was suspended in isopropyl alcohol (600 ml) into flask at 70-80° C. and stir for 10-15 min to get a solution, further added charge activated carbon (5.0 gm) and stir for 10 min at the same temperature. Filter the mass through hyflow bed, wash with isopropyl alcohol (100 ml) and charge purified water (14 ml) into flask. The resultant filtrate was stir at 70-80° C. for 10 min to dissolve the material, cool the mass to 25-30° C. and stir for 45-60 min. The resultant material was filter, wash with isopropyl alcohol (25 ml) and dry the material at 60-65° C. for 8 hours to obtain Pure Molnupiravir.

Yield: 79.21% (70.5 gm)
Purity: 99.81%

Example 5

Crude Molnupiravir (91.0 gm) was suspended into isopropyl alcohol (600 ml) and stir the reaction mass at 70-80° C. for 10-15min to dissolve the material, followed by addition of activated carbon (5.0 gm) and stir for 10 min at the same temperature. The obtain mass was filter through hyflow bed and wash with isopropyl alcohol (100 ml). The obtain filterate was concentrated under reduced pressure at below 60° C., further added ethyl acetate (200 ml) into mass, stir the mass for 10-15 minutes at 60-65° C. and allow cooling 25-30° C. The resultant mass was stir for 45-60 min to obtain material was filtered, washed with ethyl acetate (25 ml) and dried at 60-65° C. to get pure Molnupiravir.

Yield: 76.63% (68.2 gm)
Purity: 99.75%.

Example 6

Crude Molnupiravir material (91.0 gm) were added to isopropyl alcohol (600 ml), stir the mass at 70-80° C. for 10-15 min to dissolve the material. Charge activated carbon (5.0 gm) and stir for 10 min at the same temperature. Filter the mass through hyflow bed and wash with isopropyl alcohol (100 ml). Concentrate the reaction mass under reduced pressure at below 60° C., further added purified water (200 ml) into mass and stir the mass for 10-15 min at 60-65° C. Cool the mass to 25-30° C. and stir the mass for 45-60 min. Further cool to 0-5° C. and stir for 20-30 min at the same temperature. The resultant material was filter, washed with chilled purified water (25 ml) and dry the material at 60-65° C. to get pure Molnupiravir.

Yield: 68.08% (60.6 gm)
Purity: 99.79%.

Example 7

Crude Molnupiravir material (50.0 gm) were added to purified water (150 ml), stir the mass at 70-80° C. for 10-15 min to dissolve the material. Charge activated carbon (2.50 gm) and stir for 10 min at the same temperature. Filter the mass through hyflow bed and wash with purified water (25 ml). Cool the mass to 25-30° C. and stir the mass for 45-60 min. Further cool to 0-5° C. and stir for 20-30 min at the same temperature. The resultant material was filter, washed with chilled purified water (25 ml) and dry the material at 60-65° C. to get pure Molnupiravir.

Yield: 91% (45.5 gm)
Purity: ≥99.5%

Example 8

Amorphous of Molnupiravir

Molnupiravir (25 g) was dissolved in 250 mL of ethylacetate it was warmed back to 70° C. and distilled out completely till solid precipitates, added hexanes allowed to cool slowly to rt with stirring for 4 hrs, solid that formed was filtered, washed with hexanes and dried at 50° C. under vacuum for 18 hours. Obtained pure (22 g) Amorphous of Molnupiravir.

Example 9

Molnupiravir (25 g) was dissolved in 250 mL of Ethyl alcohol and spray dried at 50°. solid that formed was pure (22 g) Amorphous of Molnupiravir.

We claim:
1. A process for the preparation of pure crystalline form of Molnupiravir, the process comprising:
    a) dissolving Molnupiravir in a solvent at 55 to 60°,
    b) optionally adding water,
    c) cooling to 25-30° C., and
    d) filtering precipitated solid to obtain pure crystalline form of Molnupiravir.
2. The process according to claim 1, wherein the solvent is ethyl acetate water.
3. An amorphous form of Molnupiravir.
4. An amorphous form of Molnupiravir according to claim 3, having a powder X-ray powder diffraction pattern substantially in accordance with FIG. 5.
5. A process for the preparation of pure amorphous form of Molnupiravir according to claim 3, the process comprising:
    a) dissolving Molnupiravir in a solvent at 50-80° C.,
    b) distilling out the solvent or spray drying, and
    c) isolating pure amorphous form of Molnupiravir.

6. The process as claimed in claim 5, wherein the solvent in step-a) can be selected from the group consisting of ethylacetate, ethyl alcohol, and dichloromethane.

* * * * *